(12) United States Patent
De Godzinsky

(10) Patent No.: US 8,149,990 B2
(45) Date of Patent: Apr. 3, 2012

(54) WIRELESS INTRA-ORAL X-RAY IMAGING

(75) Inventor: Christian De Godzinsky, Vanda (FI)

(73) Assignee: Planmeca Oy, Helsinki (FI)

( * ) Notice: Subject to any disclaimer, the term of this patent is extended or adjusted under 35 U.S.C. 154(b) by 1127 days.

(21) Appl. No.: 11/572,487

(22) PCT Filed: Jul. 22, 2005

(86) PCT No.: PCT/FI2005/000337
§ 371 (c)(1),
(2), (4) Date: Jan. 22, 2007

(87) PCT Pub. No.: WO2006/008339
PCT Pub. Date: Jan. 26, 2006

(65) Prior Publication Data
US 2007/0286335 A1 Dec. 13, 2007

(30) Foreign Application Priority Data
Jul. 22, 2004 (FI) .................................... 20041008

(51) Int. Cl.
A61B 6/14 (2006.01)
G01N 23/04 (2006.01)
H01L 27/146 (2006.01)

(52) U.S. Cl. ........ 378/62; 378/38; 378/191; 250/370.09

(58) Field of Classification Search .................... 378/38, 378/62, 91, 98.8, 189, 191; 250/370.01, 250/370.04, 370.08, 370.09, 370.14
See application file for complete search history.

(56) References Cited

U.S. PATENT DOCUMENTS

| 4,223,228 | A | 9/1980 | Kaplan |
| 5,454,022 | A | 9/1995 | Lee-Teh et al. |
| 5,463,669 | A | 10/1995 | Kaplan |
| 5,514,873 | A | 5/1996 | Schulze-Ganzlin et al. |
| 6,404,854 | B1 * | 6/2002 | Carroll et al. ................ 378/98.8 |
| 7,117,033 | B2 * | 10/2006 | Shalev et al. ..................... 607/2 |
| 2004/0066898 | A1 * | 4/2004 | Schick et al. ................ 378/98.9 |
| 2004/0188625 | A1 | 9/2004 | Schulze-Ganzlin |
| 2005/0041144 | A1 | 2/2005 | Mitchell et al. |
| 2005/0134461 | A1 | 6/2005 | Gelbman et al. |
| 2005/0143624 | A1 | 6/2005 | Iddan |
| 2005/0220272 | A1 * | 10/2005 | Glazer ......................... 378/168 |
| 2005/0254625 | A1 * | 11/2005 | Schick et al. ..................... 378/98 |

* cited by examiner

Primary Examiner — Anastasia Midkiff
(74) Attorney, Agent, or Firm — Cozen O'Connor

(57) ABSTRACT

This invention relates to x-ray imaging, especially to an imaging arrangement used in intra-oral x-ray imaging, to a wireless imaging sensor and to a base station for the sensor as well as to methods for supplying operating power to the sensor and transmitting information to the sensor and from the sensor wirelessly, in which invention such a wireless power transmission link is used, which is arranged to be used for supplying energy to the sensor in connection with the imaging process.

29 Claims, 6 Drawing Sheets

WIRELESS INTRA-ORAL X-RAY IMAGING

FIELD OF THE INVENTION

The present invention relates to X-ray imaging, especially to an imaging arrangement used in intra-oral X-ray imaging, to a wireless image sensor and a sensor base station pertaining to it, and to methods for supplying operating power to a sensor and for transmitting data to and from a sensor wirelessly.

BACKGROUND OF THE INVENTION

Intra-oral X-ray images are taken by using an X-ray examination apparatus which typically includes, on the one hand, a multi-jointed arm construction and a radiation source arranged in connection with it and, on the other hand, an image-data receiving means to be positioned within the patient's mouth in a desired orientation. Generally, electric imaging sensors, which are based on e.g. charge coupled device (CCD) or complementary metal oxide semiconductor (CMOS) technologies, have increasingly emerged along with the use of traditional film.

In order to enable electric intra-oral imaging, one should be able to, for the first, supply the operating power required by the sensor to be positioned within the mouth and, for the second, transfer the image data detected by the sensor to storage or e.g. onto a display. Furthermore, one must be able to identify in some way the moment of beginning of the imaging at least, i.e., the beginning of irradiation. In the earliest electric intra-oral X-ray arrangements cords were used not only for supplying electric energy but also, inter alia, for transmitting signals for synchronising operations of the radiation source and the sensor. Since, solutions have been developed in which e.g. the beginning of irradiation may be identified based on a signal received directly from the sensor, whereby the synchronisation of the operations of the sensor and the radiation source via a cable has not been necessary any more. However, the sensor cable was still required for, on the first hand, supplying electric power and, on the other hand, e.g. transmitting image data and sensor control information.

In intra-oral X-ray imaging, the sensor has to be repeatedly positioned into different positions within the patient's mouth. In this context the sensor cord bends, whereby the cord itself and its connection to the sensor are repeatedly subject to such forces, which will readily wear out the cord and especially its connection to the sensor. It is quite typical that the lifetime of the cord will be shorter than the one of the sensor itself. Although in intra-oral imaging arrangements the cord as such may, when arranged to be of suitable length, provide a safety means for lessening the possibility of the relatively expensive sensor dropping onto the floor and thus getting broken, one has begun in the field of intra-oral X-ray imaging, as there has been done in many other fields as well, developing solutions based on wireless technology.

From the viewpoint of the practical realisation of a wireless intra-oral sensor, an essential characteristic of the sensor is its low power consumption. As it earlier has been possible to achieve diagnostically adequate image quality only with CCD sensor technology, characteristic features of which being fairly high power consumption and complex electronics—not the least because of the several different voltage levels required, a wireless intra-oral X-ray arrangement was not possible to be realised in practice until development of other technologies, such as CMOS sensors, had reached a sufficiently high level.

A limiting condition of intra-oral X-ray imaging is also the sensor size which cannot, for understandable reasons, be very large both for its surface area and its thickness. On the first hand, one must be able to supply in any case the operating power required by the sensor positioned within the patient's mouth and, on the other hand, transfer the image information detected by the sensor to a display or for storage. In addition, it would be preferable if one would be able to transmit e.g. control signals in the direction of the sensor.

Thus, in the electric intra-oral sensors of the first-generation the transfer of data and power was realised via cables, as the technology was not advanced enough for wireless data transmission or, overall, for using wireless technology. Wireless arrangements developed since are typically based on using such a base station in which a battery or a capacitor arranged to the sensor is charged either via a physical electric connection to be arranged between the base station and the sensor or by means of induction current. Also replaceable batteries may be used in the sensors. At least a radio frequency (RF) link has been used for transmitting data from the sensor. As far as these prior art solutions are concerned, a reference may be made to e.g. U.S. Pat. No. 6,527,442 and Japanese published application 2003-79617. The latter of these, for example, describes an imaging arrangement intended to be used in intra-oral X-ray imaging in which a battery or a rechargeable battery, used as the power source of the sensor, is placed in a holder unit outside the sensor, which holder unit is connected to the sensor via a cord. The rechargeable battery may be charged in the base station of the holder unit. Image data may be transmitted from the sensor via the holder unit either when it is connected to its base station or wirelessly by radio technology. The wireless data transmission may be arranged either between the sensor and the base station, or to occur directly together with a personal computer e.g. by Bluetooth technology. If the battery can be realised small enough, it may be placed within the sensor, too.

Wireless digital intra-oral sensors on the market today have certain characteristics which would be nice to get rid of or be able to be improved. For the first, using batteries as power source of the sensor causes, besides the bother and cost of changing the battery from time to time, also the fact that it is almost impossible, in practice, to arrange the sensor hermetically sealable in order to enable its cold-sterilisation (immersing it into a liquid). Lifetime of rechargeable batteries is limited, too, and when using either of them, the sensor inevitably becomes substantially large. For the second, a rechargeable battery or a capacitor must be repeatedly re-charged, whereby one may find oneself in situations in which one has to wait for the sensor to get charged to be ready for imaging—especially when the imaging arrangement should, for reasons of radiation hygiene to begin with, be realised such that the imaging cannot be initiated even, if it is possible that the energy stored in the sensor is not enough for being certain that the picture can be taken and either saved in the sensor itself or sent forward.

The small sensor size required in intra-oral imaging is problematic also from the viewpoint of wireless data transmission, because RF links realisable with current technology that would enable quick enough transmission of image information and especially bidirectional data transmission are relatively large and require reasonably much power. Using bidirectional RF links also requisites reasonably complicated electronics. On the other hand, if data transmission from the sensor is arranged only unidirectional, e.g. by sending image information from the sensor to the receiver in real time, re-transmitting the image is not possible in case needed but one has to simply trust that there are no disturbances in the data transmission. In data transmission realised by radio frequencies, disturbances may be caused by e.g. the lengthy data transmission distance from the sensor in the patient's mouth (through soft tissue) to the receiver and both GSM phones and other radio transmitters operating at high frequencies (>10 MHz) (Bluetooth, WLAN) or other radio-frequency devices of high-power. In case the power of the power source is not, for some reason, sufficient for performing the imaging event as a whole and transmission of image data is only possible in real time, one may have to repeat the whole imaging.

There may be a need to use a plurality of sensors in the same premises. When using radio frequencies, one might have to use e.g. different frequencies or one has to arrange selectable transmission channels to the sensors for realising undisturbed data transmission. Even then one must in any case be able to manage in some manner which frequency or channel can be used at a given time.

An object of the present invention, with its preferable embodiments, is thus to offer possibilities for decreasing or avoiding many of the above-described problems and limitations. Especially, an object of the invention is to decrease the problems related to wireless intra-oral imaging based on batteries, on one hand, and on rechargeable batteries or other components to be charged beforehand for imaging, on the other.

BRIEF DESCRIPTION OF THE INVENTION

The essential characteristics of the invention are presented in the accompanying patent claims. In the different embodiments of the invention there is no need to charge the image sensor to be ready for imaging beforehand, but the energy required for its use is supplied to the sensor in connection with the actual imaging event. The sensor is arranged to be used without a physical contact to any electric power or data transmission bus and to be activated when it is brought to the operating range of a wireless power transmitter. Preferably, the transmitter sending energy wirelessly to the sensor is integrated with e.g. the source of radiation, whereby when the corresponding receiver is located in the sensor, the arrangement may be realised e.g. in such a way that irradiation is possible only when the sensor is located in the range of the power transmission link in question, which range is arranged short.

The invention with its preferable embodiments will facilitate the work stages of the dental care personnel external to the actual imaging, as one does not have to take care of changing batteries nor charging the sensor beforehand prior to the imaging event.

An intra-oral sensor according to the invention may be realised without any lids or slots as hermetically sealed, which enables its sterilisation by immersing in the sterilising liquid, too.

The imaging arrangement may preferably be realised so that an inductive transmitter is used in power transmission, which transmitter may also be used for supplying data to the sensor. It is also possible to utilise the magnetic field produced by the inductive transmitter in positioning the sensor to a desired position with respect to the X-ray beam produced by the radiation source.

When arranging the sensor to be operable only in the essential proximity of the power transmitter one may use such an RF link for transmission of image data from the sensor in which the power of the transmitter is considerably low. Further one may accomplish a good immunity against disturbances caused by other devices, such as GSM phones, by using directional antennas and by arranging the receiver of the RF link quite insensitive and/or by placing it inside a beam limiter (of metal) of the X-ray source. Thus, an embodiment of the invention enables a solution in which the data transmission may operate reliably in different operating conditions and more than one sensor may be used within the same space without them necessarily disturbing each other's operation.

Especially, the invention enables implementation of the sensor in a relatively small size but, despite of that, as capable of receiving and sending information wirelessly in its imaging position, i.e., to communicate bidirectionally.

Other objects and some preferable embodiments of the invention will be described in the following in more detail with the aid of the accompanying figures as well. In the following and in the above, when using terms "energy" and "power" in the context of this application is meant, in practice, the same thing, i.e., the "energy" or the "operating power" which must be available for the sensor in connection with the imaging event for enabling imaging.

DETAILED DESCRIPTION OF THE INVENTION

Figure 1:
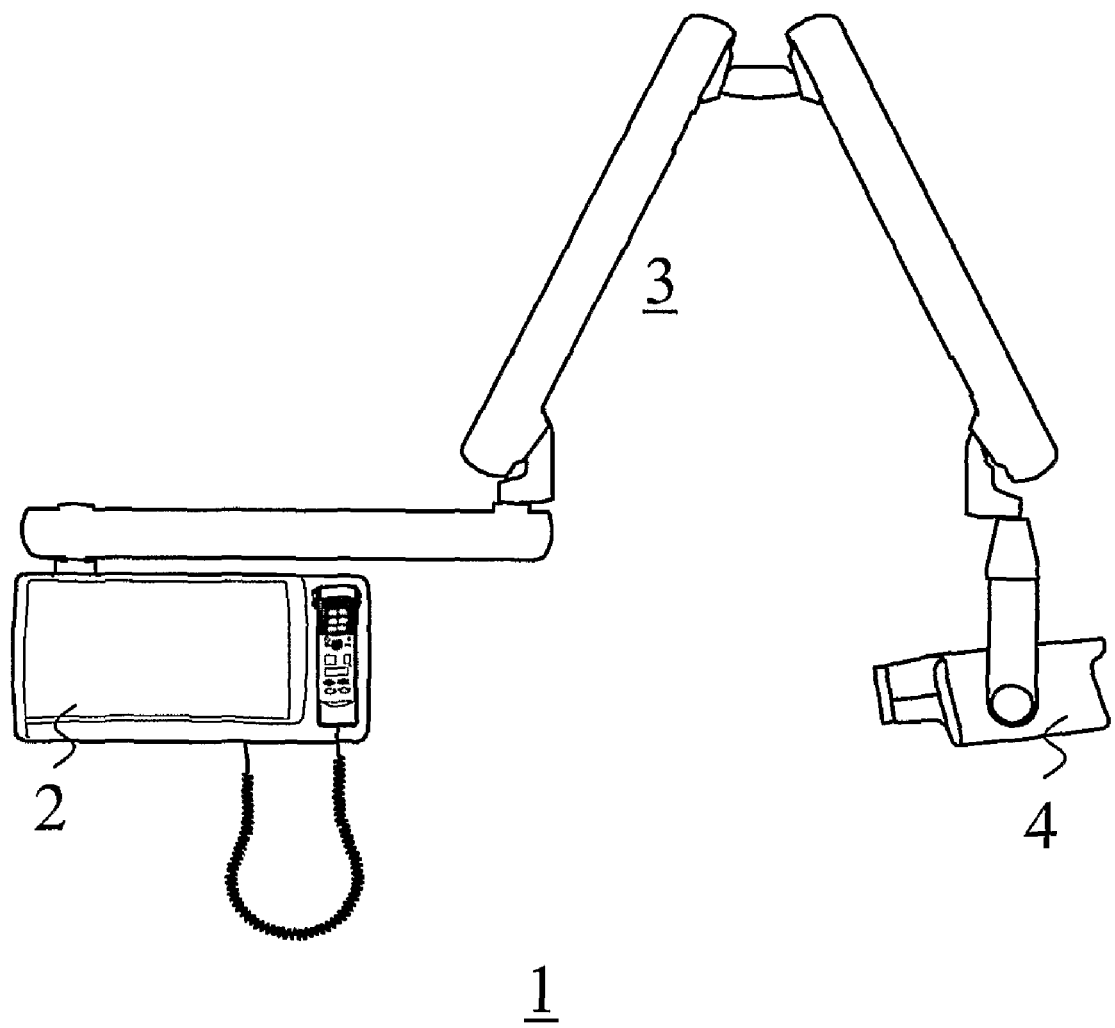
FIGS. 1, 2a and 2b show a typical intra-oral X-ray device.
Figure 2:
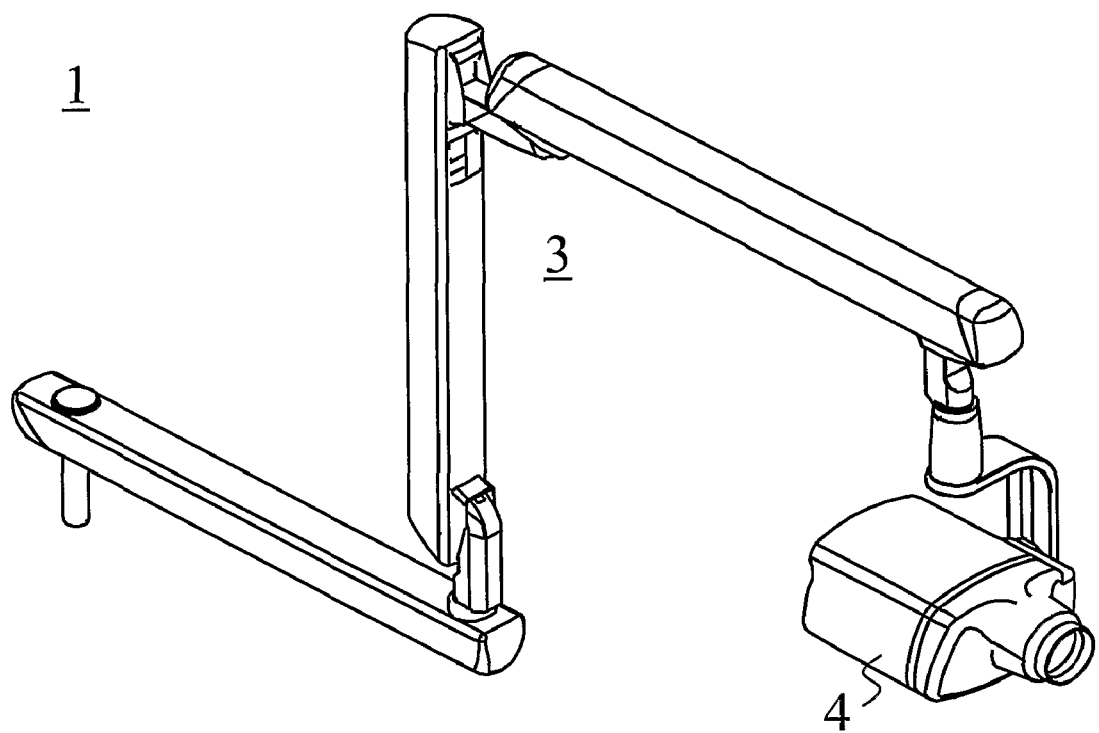
Figure 2:
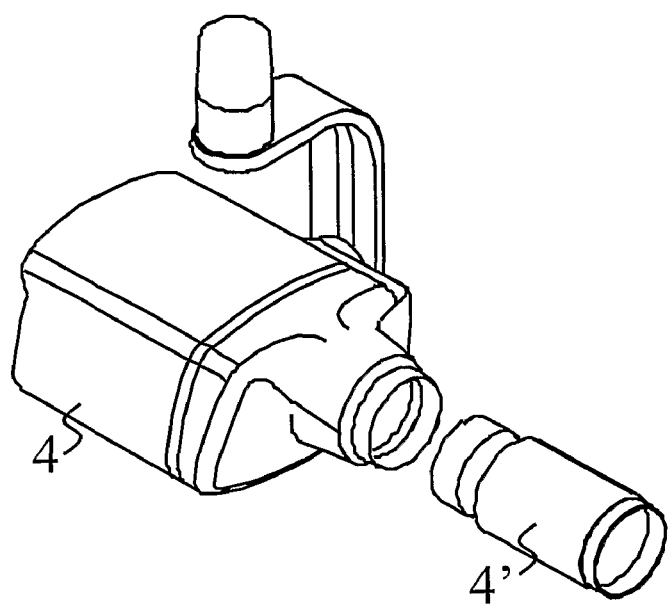

FIGS. 1, 2a and 2b show a typical intra-oral X-ray device (1) which includes a control panel (2), a jointed arm construction (3) and an X-ray source (4). FIG. 2b shows additionally an elongated collimator (4') which may be attached to a housing of the X-ray source (4) for limiting the X-ray beam more precisely and thus minimising the radiation dose received by the patient. The multi-element arm-joint constructions (3) of intra-oral X-ray devices create a lot of degrees of freedom for positioning the X-ray source (4) in a desired manner.

Figure 3:
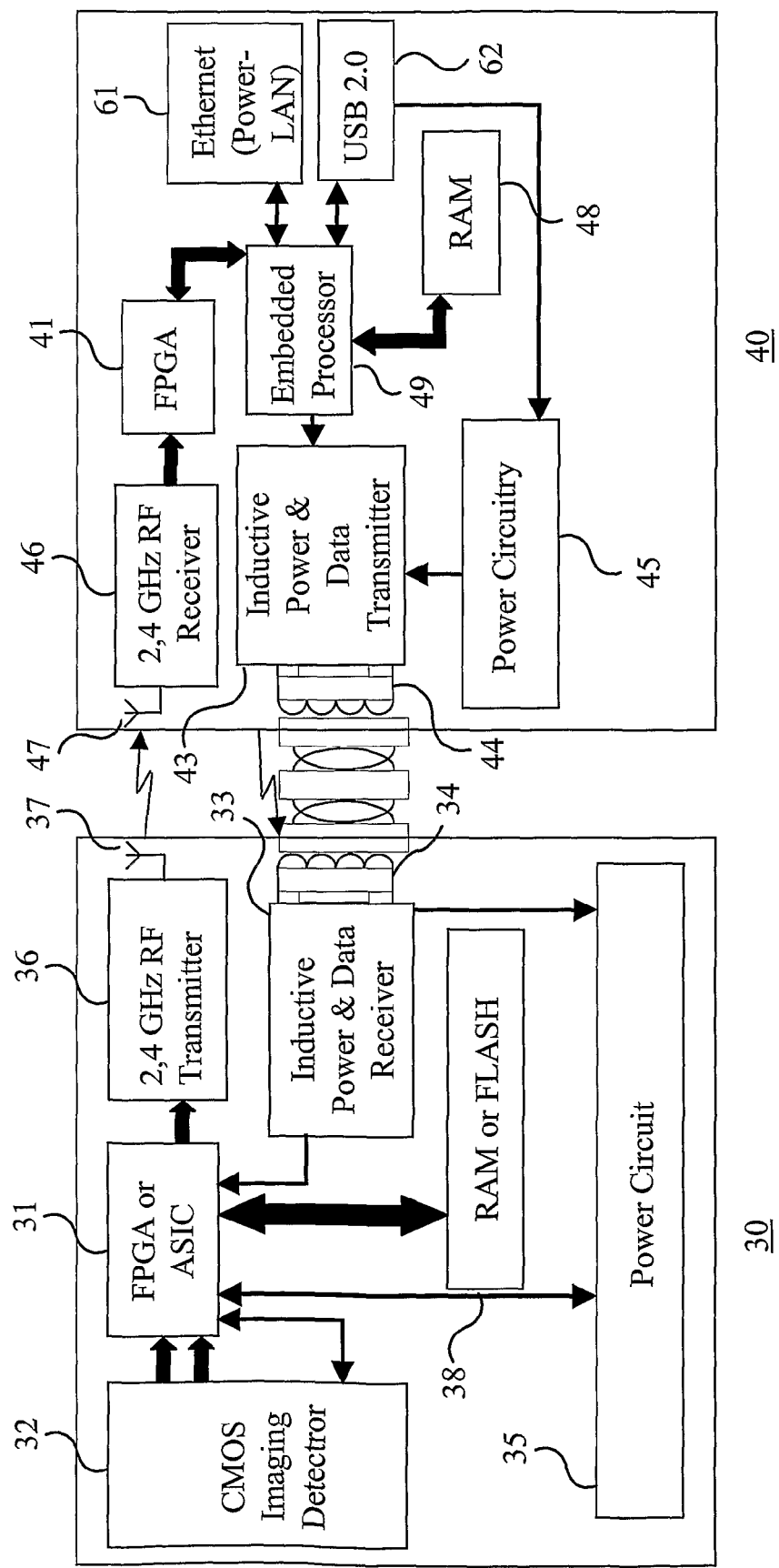
FIG. 3 shows components of a sensor and its base station suitable to be used in the imaging arrangement according to the invention.
Figure 4B:
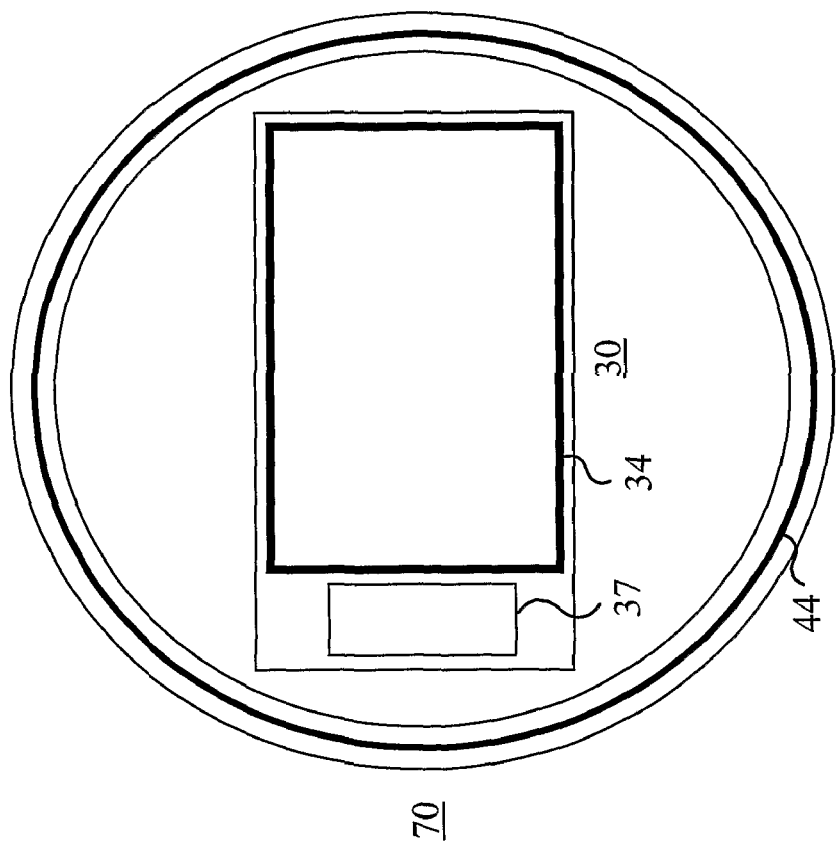
FIGS. 4a and 4b show an arrangement according to the invention for realising transmission links.
Figure 4A:
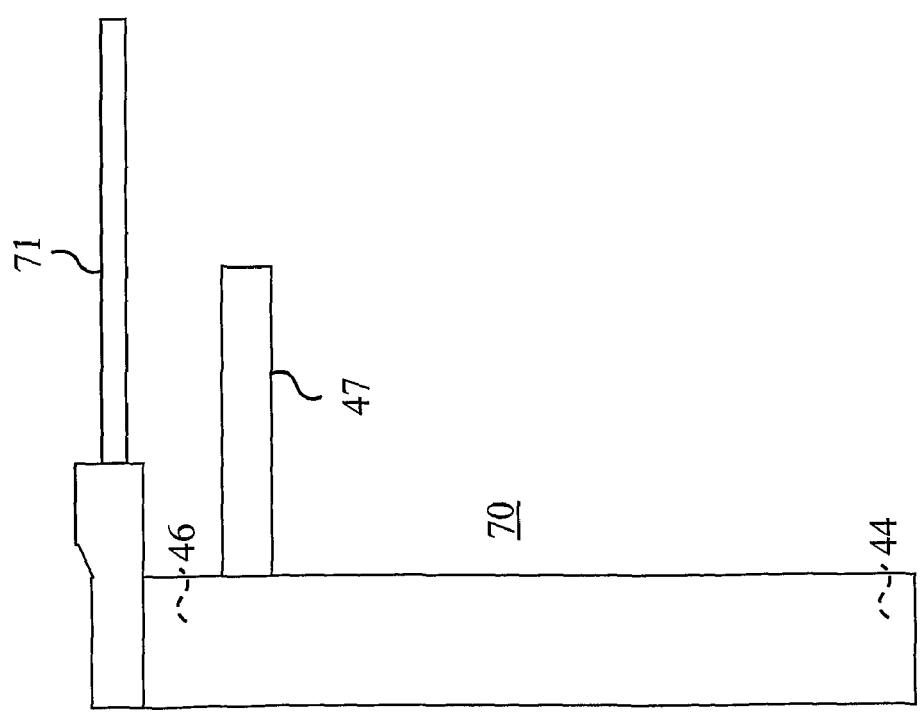

FIG. 3 shows components of a sensor (30) and a base station (40) suitable to be used in the imaging arrangement according to the invention. FIGS. 4a and 4b illustrate, for their part, by means of examples how transmission links (33, 43; 36, 46) used in the invention and shown in FIG. 3 may be arranged to an intra-oral X-ray device (1) according to FIGS. 1, 2a and 2b.

The sensor (30) according to FIG. 3 includes an FPGA (field programmable gate array) or an ASIC (application specific integrated circuit) circuit (31) controlling its different functions and a CMOS detector (32). The energy required by the sensor (30) is supplied via a wireless transmission link (33, 43), which in the embodiment according to FIG. 3 comprises, on the side of the sensor (30), a receiver (33) of an inductive-link including a coil (34). The coil (34) of the inductive receiver (33) may be arranged e.g. as in the shape of a rectangle so that it essentially imitates the shape of the sensor (30) perimeter and is located in the essential proximity of at least part of the sensor (30) edges. The coil (34) is preferably arranged in connection with the sensor housing so that the winding will not limit the active detector surface available in the sensor. The receiver (33) to be arranged to the sensor may also be e.g. an RF receiver or other corresponding component receiving energy wirelessly and not being electrically chargeable.

The power supply circuit (35) as such belonging to the sensor (30) may include e.g. small capacitors used in transmitting electric power received from the induction receiver (33) but, according to the invention, the sensor electronics does not include any such component which could be used for storing energy supplied to the sensor (30) beforehand and thus enabling its use without the "on-line power supply" performed in connection with the imaging event via the wireless transmission link (33, 43). The receiver of the transmission-link (33) arranged to the sensor (30) is therefore the primary power source supplying current to the sensor electronics, and the energy storing capacity of the components possibly belonging to the power supply circuit (35) being capable of storing energy is in any case lower than the electric power required by the sensor electronics in connection with an individual imaging event. For example, when considering intra-oral sensors of today, i.e., taking into account, inter alia, the detector sizes typically used, e.g. the RF technology used for transmitting image data and the capacitor technologies available, this would mean total energy storing capacity of a capacitor or capacitors possibly belonging to the sensor electronics of below 20 Ws, e.g. below 5 Ws, in practice, easily even an energy storing capacity of less than 1-2 Ws.

The detector (32) used in the sensor (30) may be monolithic and at least part of the actual sensor electronics may be integrated with it so that already the output from the detector is e.g. in 12-bit digital form. Even though part of the active detector area will be lost as a consequence of such increase of electronics, the loss may be minimised by arranging the main portion of the components to one end of the detector (32) and to the other three sides only that portion of the electronics which is necessary. In case CMOS technology is used, the power requirement of the sensor (30) is relatively low. With advancing technology, it is presumable that one will be able to integrate the whole FPGA or ASIC circuit (31) with the detector (32). On the other hand, with advancing detector technology it is presumable that a sensor with such preferable characteristics which are presented as advantages of the CMOS technology here when using it in an application according to this invention will be realisable also with other solutions than the ones based on CMOS technology.

Image information is transmitted from the sensor according to FIG. 3 by an RF transmitter (36) of 2.4 GHz, either essentially in real time as image data is detected on the detector (32) (so-called streaming mode) or essentially immediately after the image has been taken. It is possible to arrange e.g. a RAM (random access memory) or a FLASH memory (38) to the sensor (30) for temporarily storing the detected image, whereby it can also be re-sent in case so required. The size of the memory may be arranged to enable storing of either the image data as a whole or only part of it. In the latter case, the imaging arrangement is preferably implemented so that there has been arranged a means to the base station (40) for identifying the data packets possibly damaged in transmission and a means for transmitting information of this quickly to the sensor (30). This is possible e.g. by using the energy transmission link (33, 43) for this data transmission and by arranging the speed of it to be sufficient. In even more general terms, thus, the energy transmission link (33, 43) may be used for transmitting to the sensor (30) both energy and information.

FIG. 3 shows also a preferable solution for a base station (40) according to the invention. In the context of this invention, a base station means primarily a functional entity which may be arranged not only as a single physical unit, but its components or part thereof may also be integrated partly or completely with other construction(s) or device(s), such as a radiation source or an image processing device. The energy needed for operating a sensor (30) in connection with an imaging event is transmitted to it via the inductive transmitter (43) of the base station (40) shown in FIG. 3. As already referred to above, the inductive link (33, 43) may also be used for data transmission in the direction of the sensor (30). Then again data, such as image and status information that has been transmitted by the sensor (30) will be received at the RF receiver (46) arranged to the base station (40). By arranging to the imaging arrangement bidirectional data transmission according to FIG. 3 by means of, first, an unidirectional RF link (36, 46), and second, an inductive link (33, 43) one will be able to use unidirectional RF links which are considerably smaller and simpler than bidirectional RF links that, for its part, enhances possibilities for realising the sensor (30) as small in size.

It is possible to implement the invention so that significantly lower data transmission speed is used for sending control data to the sensor (30) than what is required in practice for transmitting image data from the sensor (30), but also e.g. an inductive link (33, 43) may be realised such that also a high-speed data transmission is enabled. Then, it can be utilised e.g. in the above-described manner for transmitting error messages to the sensor (30) while image data is being transmitted in a situation in which one of the transmitted data packets has been damaged. Data transmission errors are actually not a real problem when such a large memory (37) is arranged to the sensor (30) that the whole image data may be re-transmitted in case needed, but by arranging the data transmission connections such that information of the damaged data packet will be transmitted to the sensor (30) in time, in view of enabling re-transmission of the data packet still in the memory (38), it is sufficient to use also a smaller memory.

The base station (40) according to FIG. 3 also includes a base-station power supply circuit (45), an FPGA circuit (41) transmitting image data to the processor (49) of the base-station and a memory (48) functioning in connection with the processor, which memory enables temporary storing of image-data received from the sensor (30). In addition, there has been arranged Ethernet and/or USB (Universal Serial Bus) user interfaces (61, 62) to the base station (40) via which one is able to connect e.g. to an image processing device, a patient management system of a dental clinic etc. connected to a local area network. Furthermore, the base station may be arranged with a data transmission connection, not shown in FIG. 3, via which the operation of the radiation source (4) and the sensor (30) may be synchronised, if so desired, such that the control system of the imaging arrangement is arranged to prevent use of the radiation source (4) unless the sensor (30) used in imaging is located within the operating range of the power transmission link (33, 43), i.e., unless the sensor (30) is ready to receive radiation including image information. Naturally, the components of a base station (40) according to or corresponding to that of FIG. 3, or part thereof may also be e.g. an integrated part of electronics of a radiation source (4) or be divided physically to even more than one unit.

In the arrangement according to the invention, the base station (40) may take the power it requires from the bus (PowerLAN, USB) via which image data is transmitted forward to a personal computer (PC) or a data network, whereby one avoids using an external power source needed for this purpose only. There may be circumstances, though, in which such a preferable and simple solution is not adequate, in light of which the base station (40) may be provided with a connection of its own for an external power source.

FIGS. 4a and 4b, especially FIG. 4a, illustrate one preferable embodiment of the invention in which the coil (44) of the inductive transmitter (43) and the RF receiver (46) together with its antenna (47) have been physically separated from the actual base station (40) to form an adapter or a transponder (70) of e.g. circular or rectangular form and being connectable to the X-ray source (4), e.g. to a collimator (4') attached thereto, and being connected to the electronics of the actual base station (40) via a cord (71). The RF receiver (46) with its antenna (47) shown in FIG. 4a has been left out of FIG. 4b for simplicity's sake, and FIG. 4b has been correspondingly complemented compared to FIG. 4a to show also how the sensor (30) would be typically positioned in connection with an imaging event with respect to the transponder (70) according to FIG. 4a. So, if also the sensor (30) and e.g. the collimator (4') of the radiation source (4) were drawn in FIG. 4a, the sensor (30) would be located to the left of the transponder (70) and the collimator (4') would converge to the transponder (70) from the right.

In the embodiment according to FIGS. 4a and 4b the coil (44) of the inductive transmitter (43) is thus arranged within a ring-shaped adapter or transponder (70), and also the antenna (47) of the RF receiver (46) and its preamplifier (not shown in the figures) are integrated with the adapter (70). The adapter (70) may be attached to the end of e.g. an X-ray tube head (4) or a collimator tube (4') used in it. In such an arrangement, the transmission links (33, 43; 36, 46) will always become positioned to roughly the same distance, such as around 2-8 cm, and in the same direction with respect to each other in connection with imaging when the imaging arrangement (50) is ready for imaging, i.e., when the intra-oral sensor (30) is positioned in the patient's mouth and the X-ray source (4) is located in its corresponding imaging position. Inter alia, in such embodiment of the invention, one is able to use directional antennas (37, 47) for transmitting image data which, for its part, improves noise immunity of the data transmission system. It is also possible to place the antenna (47) of the RF receiver inside the collimator tube (4') in order to protect it from external sources of disturbances. When, in addition, the distance of data transmission between the RF link (36, 46) antennas (37, 47) will therefore be short, the transmission power it requires will also be low. The data transmission distance is thus in practice e.g. less than 15 cm, such as in the order of 2-8 cm. It is possible to arrange the RF receiver (46) receiving image information less sensitive and thus make the data transmission relatively immune to the effects of possible sources of disturbances. The short transmission distance also enables that interference will not be created from the other sensors possibly being in use and thus there is no need to code the sensors to different channels.

Concerning the energy transmission, the intra-oral X-ray imaging arrangement according to the invention is preferably realised such that in connection with the imaging situation the transmitter (43) supplying energy to the sensor (30) is arranged to always become positioned in the essential vicinity of the sensor (30) positioned in the patient's mouth. Such positioning objects are e.g. a holder arranged on the patient's neck, ear or a band on his/her forehead or a corresponding item, or e.g. on the headrest of the dental chair or, as said, the X-ray source (4) itself.

In connection with intra-oral X-ray imaging one typically aims to collimate (limit) the X-ray beam to correspond the shape and size of the image-data receiver used and to position the image-data receiver at the centre of the beam; this situation being illustrated also in FIG. 4b. One preferable embodiment of the invention thus comprises an arrangement in which the inductive transmitter is placed within the X-ray source and in which small receiver coils are arranged e.g. essentially to the corners of a sensor (30) of essentially rectangular shape, or to at least one of them. When the sensor (30) is being positioned with respect to the radiation source (4)—or in connection with intra-oral imaging, more frequently perhaps vice versa, when the X-ray source is being positioned with respect to the sensor—the signals received from the coils change according to how their position changes in the magnetic field produced by the inductive transmitter (43) attached to the X-ray source (4). These signals may be arranged to be sent e.g. via the RF link (36, 46) as signals indicating the relative positions of the sensor (30) and the X-ray source (4), which signals may be utilised in achieving the desired relative position of the sensor (30) and the radiation source (4). Naturally, it is possible to receive more data from several of such coils compared to only one coil. However, it is possible to arrange a corresponding signal from a receiver (33) of the inductive link (33, 43) only, which receiver essentially circles the edges of the sensor (30), whereby even it alone can be used to facilitate in positioning the sensor.

The wireless data transfer of intra-oral imaging may thus be realised so that e.g. a sensor including a CMOS detector will communicate wirelessly bidirectionally with a base station into which base station, or into functional connection thereof is also arranged a means for wireless energy transmission. In connection with imaging, the energy required for data transmission and for operation of the sensor in general is supplied to the sensor by bringing a transmitter supplying energy and a sensor comprising a corresponding receiver within the operating range of the link formed by them, preferably into the essential vicinity of each other, such as within an operating range arranged to be of less than 50 cm, preferably less than 15 cm, such as 2-8 cm. Then, when the sensor in itself has no such energy-storing components that would enable use of the sensor without energy transmission during the imaging event, it is possible to use the sensor only when it is located substantially close to the transmitter of the energy transmission link. The operating power required by the sensor is preferably transmitted inductively, whereby the inductive transmitter is preferably placed e.g. in connection with the end of the intra-oral X-ray tube head, e.g. to the tube-like part of its housing, or to the adapter to be positioned at the end of the collimator connected to it. The inductive transmitter may also be integrated e.g. as a part of the construction of the X-ray source.

In connection with the imaging event the operating system of the imaging arrangement identifies that the sensor is brought into the operating range of the power transmission link and the imaging may be started. The field of inductive power transmission may be arranged to be of relatively low frequency for minimising the possible disturbing effects it may have to the operation of the imaging sensor. The frequency used in the transmission may be e.g. essentially lower than 500 kHz, even totally of a different order of magnitude.

If the arrangement will be implemented so that the sensor will nevertheless be able to momentarily operate without continuous external energy supply, the energy transmission may be momentarily interrupted or adjusted lower in connection with the imaging event e.g. for the duration of the actual exposure, for the duration of reading image data from the detector to a memory possibly arranged to the sensor, or when sending it from the sensor to the ether. In such an application it may be preferable to implement the arrangement so that the power of the energy transmission link is arranged lower than the power taken by the (RF) transmitter link used in transmitting image data. A momentary interruption of the energy transmission may have an enhancing effect in that the power transmission taking place during an imaging event will not cause disturbances to the operation of the sensor. On the other hand, a means may be arranged to the sensor itself, too, for adjusting its power consumption at different stages of the imaging event.

Thus, according to one embodiment of the invention, it is possible to store the image data detected by the detector temporarily to a memory arranged to the sensor and to transmit it for storage from the detector after the exposure has finished, preferably as quickly as possible. This may be realised e.g. in such an arrangement in which the time the irradiation ends is known beforehand or it is identified. However, it is possible to read the signal of particularly e.g. a CMOS-type detector continuously also during the exposure. The sensor may then be arranged usable also in the so-called streaming mode, i.e., so that image data is transmitted from the sensor continuously during exposure. It will then be later possible to detect the beginning and the end of the exposure by software e.g. from the signal stored in the PC's memory. When image data is transmitted in real time at the same rate as it is read, e.g. at 300 ms intervals, there is no need to know the maximum exposure time from the viewpoint of image formation, when the data possibly causing overexposure may simply be ignored in image processing.

All in all, according to the invention, energy is supplied to the sensor essentially only in connection with the imaging event, i.e., starting a little earlier than the actual exposure is initiated, such as when positioning the imaging means for the exposure, for example, and until the image data has been managed to be transmitted from the sensor—or stored to the memory arranged in the sensor.

If image data is transmitted from the sensor only after exposure and no memory has been arranged in the sensor for storing image data, naturally, the power transmission link may not be brought outside its operating range before image data has been managed to be sent from the sensor. For preventing this, it is possible to arrange an indication light or other signal in connection with e.g. the inductive transmitter, such as to the intra-oral X-ray source in the embodiment according to FIG. 4b, which signal will indicate after the imaging that transmission of image information has been completed. When using a sensor provided with memory, it is naturally also possible to stop the transmission of the data, to do it later after imaging and/or transmit the data more than once in case the data transmission has in some way or another failed. Considering subsequent data transmission, it is possible to arrange a holder e.g. in connection with the X-ray tube, to which the sensor may be placed after imaging to enable communication with the base station arranged to the X-ray tube still after the actual imaging. In transmitting data from the sensor, a high-frequency radio transmitter and e.g. transmit power of the order of less than 1 mW are preferably used for minimising the effect of transmission on the operations of the CMOS detector and the digital electronics of the sensor.

Figure 5:
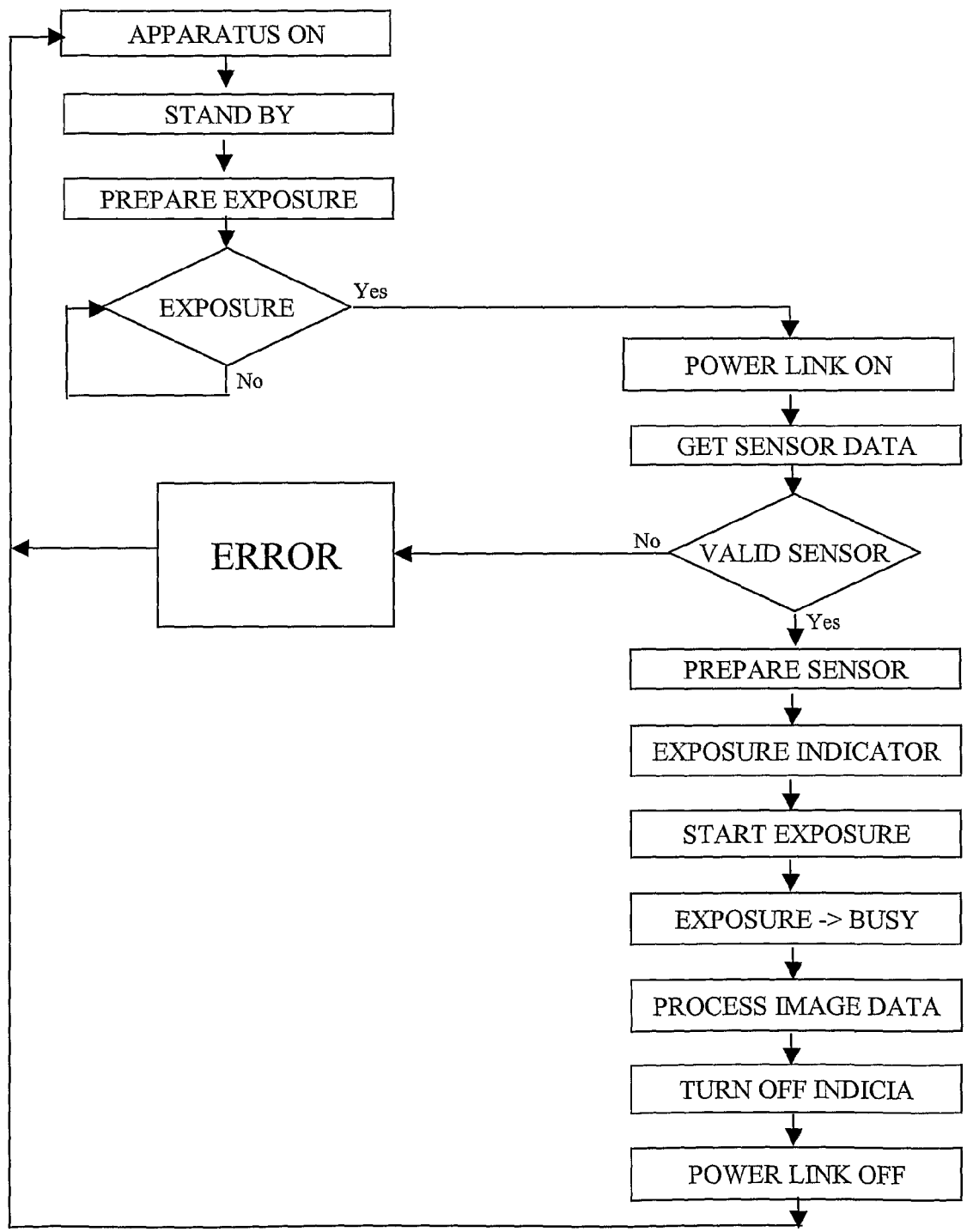
FIGS. 5 and 6 show embodiments according to the invention of methods for supplying operating power to the intra-oral sensor in connection with an imaging event.
Figure 6:
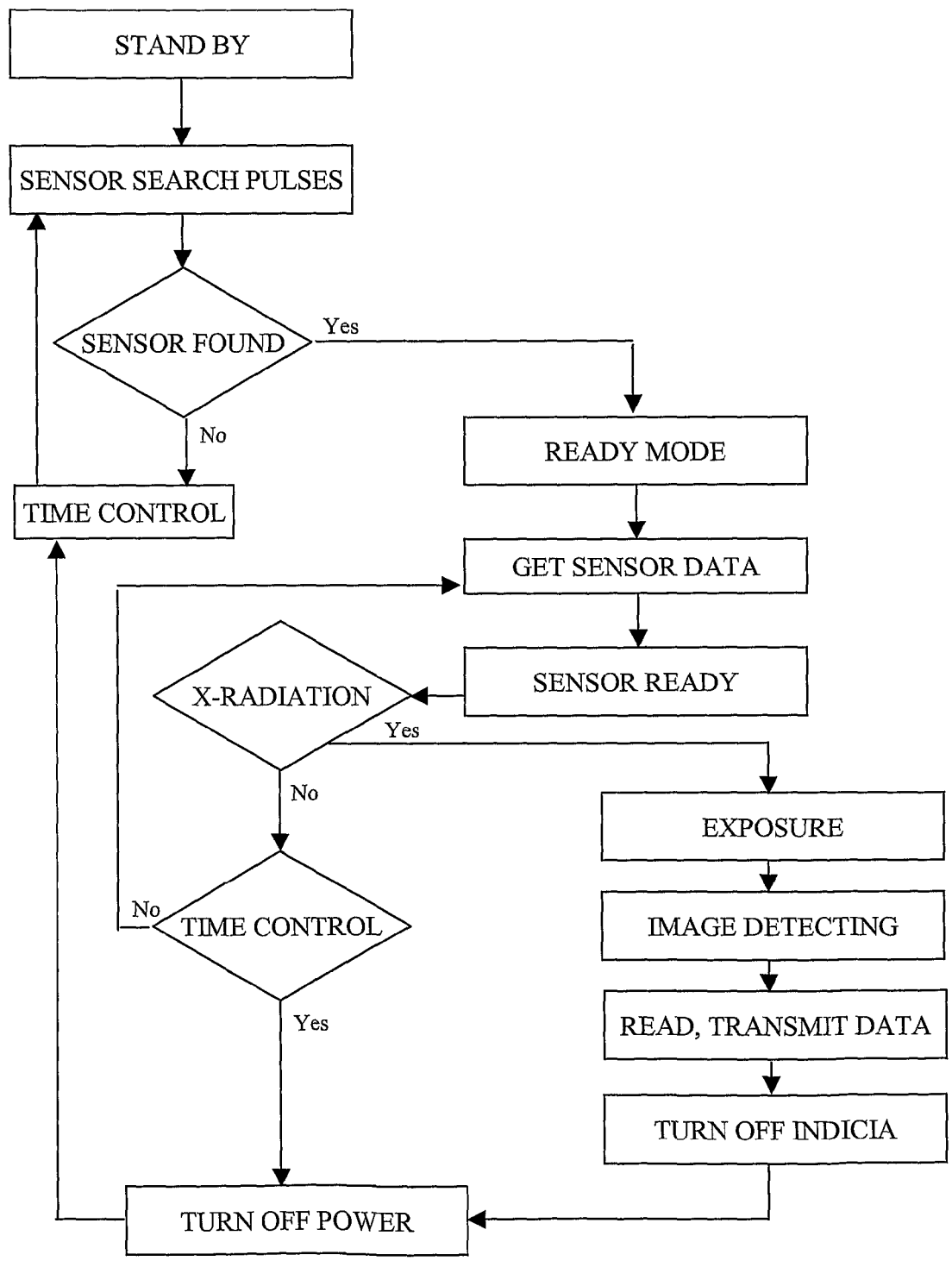

FIGS. 5 and 6 show two examples of how the invention may be applied in practise in connection with intra-oral X-ray imaging. FIG. 5 shows the use of the invention in a manner in which mutual operation of the radiation source and the energy transmission link have been synchronised. According to this embodiment, in the first stage when power of the X-ray source is turned on, the arrangement enters a STAND BY mode. The preparation stage of the imaging may include, inter alia, positioning of the radiation source, the object to be imaged and the sensor, ready for imaging. Then, when upon initiating the actual imaging an irradiation start signal is given from the exposure switch of the radiation source, the system first activates the transmitter of the energy transmission link according to the invention and checks if there is such a sensor unit within the operation range of the link which the system recognises. (As all sensors are individuals and their use requires knowledge of the sensor-specific calibration data, it is possible to use in the imaging only such sensors the repair (calibration) file of which is stored to a database pertaining to the imaging arrangement in order that one will be able to form from the image data detected by particularly that sensor in question a "real" image representing the object. With an individual serial number, it is also possible to prevent an unauthorised use of the sensor and make stealing of it pointless by user-specific opening code.) In practice, the identification of the sensor takes place so that, when being located within the operating range of the energy transmission link, the sensor sends a signal including its individual identifier via a data transmission link pertaining to the arrangement as a response to its activation. If the identifier in question is not stored to the system, i.e., if one tries to use such a sensor the databases used by the imaging arrangement do not identify, or if e.g. the respective distance between transmitter and receiver of the power-transmission-link is greater than the operating range of the link, or if the system detects some other error in the imaging arrangement, irradiation does not start and the system gives an error signal, such as a sound signal, and informs of the cause of the error. A cause of the error signal may also be e.g. inaccurate positioning of the sensor with respect to the X-ray beam produced by the radiation source.

When preconditions for a successful imaging exist, that is, inter alia, the energy transmission link transmits energy to the sensor it has identified and the sensor electronics has been activated ready for imaging, then e.g. the EXPOSURE light belonging to the arrangement is turned on, and if no exposure automatics for the imaging are included in the arrangement, irradiation of a preset duration starts. After the irradiation, the EXPOSURE light is turned off. After the exposure, the arrangement may still enter a separate BUSY mode the duration of which may depend on, for example, how transfer of the image data detected by the detector element is arranged to occur, i.e., if there is arranged a memory to the sensor via which the transfer may be done partially or as a whole also after the exposure, if there has been arranged, in connection with the transfer, feedback to transmit to the sensor information regarding data packets that may have been damaged etc. The transfer of image data may thus also be realised so that the data detected by the detector is first stored to a memory in the detector, after the imaging the sensor is transferred e.g. to a holder arranged in connection with the base station, i.e., to a position in which it is within the operating range of the power transmission link, and image data is transmitted from the sensor only at this stage. After transfer of the image data, indication lights turn off, the energy transmission link inactivates and the system returns to the STAND BY mode.

FIG. 6 shows an example of an embodiment in which the energy transmission link and the radiation source function independently with respect to each other. In this solution, the base station of the energy transmission link communicates with e.g. a PC, and when being in the STAND BY mode, the transmitter of the energy transmission link periodically sends short pulses to the ether, whereby as a response to the signal of finding a sensor within the operating range of the arrangement, the operation mode of the transmitter changes from said periodical-pulse-sending mode to an actual READY mode and the sensor is activated ready for imaging. For the sake of simplicity, in the diagram according to FIG. 6 the alternative that one would try to use some other sensor individual than such known by the system, and also other possible error situations shown in connection with the embodiment according to FIG. 5, have been omitted. If no actual exposure is done e.g. within a time preset to the system from the time the system went to the READY mode, that is, i.e., if no signal will be received from the sensor within such time of the start of irradiation, the system returns to the STAND BY mode as described above. Such a situation may occur e.g. when an exceptionally long time elapses for positioning of the sensor and the radiation source for imaging.

Detecting the start of irradiation causes a change of the status of the system to an EXPOSURE mode, during which the information detected by the detector will be integrated e.g. for a pre-determined time or until the end of irradiation is detected. If the arrangement is implemented so that the data detected by the detector is read by short intervals continuously from the detector already during the exposure, the detection of the end of irradiation may be based on an observation of a sudden fall of the detected signal level. The transmission of image data from the sensor may also be realised e.g. in some manner presented above in connection with the description of FIG. 5, after which the EXPOSURE (or BUSY) indication light is turned off and the arrangement returns to the STAND BY mode.

The invention is described here particularly in connection with its primarily preferred application, intra-oral X-ray imaging. In principle, it is possible to bring the operating power required by the sensor from outside the sensor with some other wireless technology than inductively as according to the embodiments described above, and in principle, by using only one link for transmitting both energy (and data) to the direction of the sensor and, on the other hand, for transmitting image data from the sensor. However, an arrangement according to the above-described embodiments, in which the energy is supplied to the sensor inductively and image data is transmitted in radio frequencies, respectively, enables an energy transmission/bidirectional data transmission assembly exquisitely applicable for intra-oral imaging. Then, it is also possible to construct the imaging arrangement such that the magnetic field formed by the power transmission link may also be utilised in positioning the sensor with respect to the X-ray source, as described above.

According to one preferable embodiment of the invention, the sensor data transmission is thus bidirectional and realised e.g. so that image and status data is sent from the sensor with high rate (such as at least 10 Mbit/s) with an essentially high-frequency RF transmission link of e.g. 2.4 GHz, and the sensor receives energy inductively, whereby the inductive link may also be used for slower (such as less than 9,600 kbit/s) communication in the direction of the sensor, such as for sending the sensor control signals.

The lifetime of a sensor according to the invention is long as there is no need to arrange into it any components which would be large in size, wear out when used or age or be replaceable, such as batteries or rechargeable batteries. Actually, almost the only possibility for the sensor according to the invention getting broken is a mechanical breakage caused by too a high external mechanical strains, such as a physical impact caused by the sensor dropping onto the floor or a physical impact caused by another corresponding accident. The risk of dropping onto the floor may be prevented by e.g. a safety cord and a small lug arranged to the back cover of the sensor or by other corresponding fastener arrangement. If one uses a string manufactured of thin Kevlar fibre or nylon line it can be cold-sterilised together with the sensor, or one may use disposable strings. Then, it is not necessary to use the protective bags typically used for hygienic reasons with a sensor according to the invention.

Thus, the arrangements according to the invention and its preferable embodiments provide new kinds of possibilities for implementing a wireless intra-oral sensor. For example, the use of a high-frequency and unidirectional RF link for data transmission enables a simpler sensor construction which can be realised smaller in size and the control of which is also notably simple. Because of the short transmission range, also the power consumption of the data transmission link is low, whereby also the amount of energy that has to be transmitted to the sensor is low. The use of short transmission range and a high-frequency data transmission link enable realisation of the invention without sophisticated unique application-specific arrangements, by using prior art solutions which have proven to be functional. It is also possible to arrange the data transmission channel as relatively immune to external disturbances. The components of the RF link may be realised either with discrete parts or as an integrated circuit, the use of neither disturbing the inductive link of the other direction pertaining to the arrangement when the links use essentially different frequency bands. If desired, the image data may be transmitted in real time.

With a sensor construction according to the invention, which does not include a battery, a rechargeable battery or corresponding pre-chargeable component designed for storing operating energy of the sensor, it is possible to realise the sensor as small in size, when using the sensor there is no need to repeatedly replace the battery, or charge the rechargeable battery, nor does there exist any problems caused by ageing of the rechargeable battery, taking care of servicing the sensor components, mechanical or other damages or charging the sensor between imagings. The sensor may also be realised hermetically housed and galvanically insulated, which enables its cold-sterilisation between imaging of different patients.

It is well known for a man skilled in the art that the present invention may be realised within the scope of protection defined by the accompanying patent claims also according to other embodiments than the ones presented above, inter alia, along with new possibilities offered by the advancement of detector technology.

The invention claimed is:

1. An intra-oral X-ray imaging arrangement, which includes a control system, a radiation source, an electric image data receiving sensor including sensor electronics and a wireless transmission link for transmitting at least image data detected by the sensor to a base station, to an image processing device or to some other device, a transmitter and a receiver of which transmission link being arranged, on the one hand, in connection with the sensor, and on the other hand, at least in functional connection with said base station or some other device the arrangement further including or said transmission link further being arranged to function also as a wireless power transmission link, wherein said power transmission link is structured and arranged to supply the sensor with energy only in connection with an imaging event and only after a procedure of positioning the image data receiving sensor for an exposure as part of the imaging event is initiated and wherein the sensor either includes no components capable of storing energy, or the total energy storing capacity of all components together included in the sensor electronics is lower than the energy required by the sensor in connection with an individual imaging event.

2. An imaging arrangement according to claim 1, wherein a receiver of the power transmission link is a part of the sensor electronics and wherein said receiver is arranged to function as a primary power source of a power supply circuit of the sensor electronics.

3. An imaging arrangement according to claim 1, wherein the sensor includes a component or components capable of storing energy and the total energy storing capacity of said component or components is lower than about 20 Ws.

4. An imaging arrangement according to claim 1, wherein the operating range of said power transmission link is arranged to be under about 15 cm.

5. An imaging arrangement according to claim 1, wherein a transmitter of said power transmission link is placed or arranged to be placed in a location or a position in which, when the object to be imaged and said sensor are positioned to their imaging positions according to the imaging arrangement, the sensor is positioned within the operating range of the power transmission link.

6. An imaging arrangement according to claim 5, wherein the transmitter of the power transmission link is arranged to be placed to a radiation source or to a base station arranged in essential connection with said radiation source, or to a base station attachable to the patient or arranged to a headrest of a dental chair.

7. An imaging arrangement according to claim 1, including i) a means for transmitting a signal from the sensor as a response to the sensor and the transmitter of the power transmission link being located within the operating range of the power transmission link or ii) a means for synchronising operations of said power transmission link and radiation source so that irradiation cannot be started if a control system of the imaging arrangement has no information on a receiver of the power transmission link arranged to the sensor being located within the operating range of the power transmission link.

8. An imaging arrangement according to claim 1, including i) a means for bidirectional data transmission between the sensor and a control system of the imaging arrangement, which data comprises at least control commands and image data detected by the sensor, or ii) a means to transmit during an imaging event both energy required by the sensor and control signals of the sensor.

9. An imaging arrangement according to claim 1, wherein a receiver of the power transmission link comprises a coil essentially imitating the shape of the sensor perimeter, said coil being located at least in part in the essential vicinity of the edges of the sensor, or wherein said data transmission link for transmitting at least the image data detected by the sensor is an RF link.

10. An imaging arrangement according to claim 1, wherein one or more coils are arranged to said sensor so that they are located in the essential proximity to at least one of the corners of a sensor of essentially rectangular shape, which coil or coils are arranged to transmit data on the position of said sensor with respect to a transmitter of said power transmission link in the magnetic field produced by it.

11. A wireless imaging sensor, for use in connection with intra-oral X-ray imaging, which sensor comprises a sensor housing and sensor electronics, which sensor electronics include a detector, a transmitter for transmitting at least the image data detected by said detector to the ether and a power supply circuit, wherein the power supply circuit includes a receiver of a wireless power transmission link or wherein said transmitter of image data is arranged to function also as a receiver of a wireless power trans-mission link and wherein the sensor either includes no components capable of storing energy, or the total energy storing capacity of all components together included in the sensor electronics, is lower than the energy required by the sensor in connection with an individual imaging event.

12. An imaging sensor according to claim 11, wherein said receiver of the power transmission link is an electrically non-chargeable component capable of receiving electro-magnetic energy wirelessly.

13. An imaging sensor according to claim 11, wherein a means has been arranged in the sensor for controlling the power it receives or uses in connection with an imaging event.

14. An imaging sensor according to claim 11 whose electronics include a means for receiving control data transmitted in connection with said wireless power transmission.

15. An imaging sensor according to claim 11, whose electronics include a means for storing at least part of the image data detected by the detector in a memory, either simultaneously while image data is still being detected or immediately after ending the reception of image data, or whose electronics include a means for storing at least part of the image data detected by the detector in a memory and wherein in functional connection with said transmitter for transmitting image data is arranged a means for re-transmitting the image data or a part the image data stored in said memory as a response to a control signal which is received by the sensor.

16. A base station for an intra-oral X-ray sensor, which comprises components in functional connection with each other forming a base station electronics arrangement, which components include a means wirelessly receiving at least image data from a sensor used in X-ray imaging, the base station further including a means to wirelessly transmit to the sensor energy the sensor requires in connection with an imaging event, or said means receiving image data is arranged to also function as a means which wirelessly transmits to the sensor energy the sensor requires in connection with an imaging event, wherein at least either of the means transmitting energy and the means receiving image data arranged also to function as a means which wirelessly transmits energy comprises at least one coil and/or at least one antenna attached to a mouth-opening of an X-ray source housing, or to a mouth-opening of a collimator tube attached to said housing, or to the immediate proximity of or inside said mouth-opening.

17. A base station for an intra-oral X-ray sensor, which comprises components in functional connection with each other to form a base station electronics arrangement, which components include a component wirelessly receiving at least image data from a sensor and a means to wirelessly transmit to the sensor the energy the sensor requires in connection with an imaging event, or wherein said component receiving image data is arranged to also function as a component, to wirelessly transmits to the sensor energy the sensor requires in connection with an imaging event, and wherein the base station or said component transmitting energy to the sensor is either directly or via a support means attached to or integrated into a construction which in connection with the imaging event is positioned in the essential proximity of the sensor when the sensor is positioned at its intra-oral imaging position, said support means or said construction being one of items: a headband or a collar, a headrest of a dental chair, or an X-ray source used in the intra-oral imaging.

18. A base station according to claim 16, wherein said means to wirelessly transmit energy comprises a coil which is essentially of the shape and size of the mouth-opening of said X-ray source housing or of the collimator tube attachable to it, or forms a part of an adapter integrated, attached or arranged to be attachable in the essential proximity to said mouth-opening or to the essential proximity of said mouth opening.

19. A base station according to claim 16, wherein the electronics required for using at least one of said transmitter of energy and said receiver of image data is integrated as part of the electronics of the X-ray source.

20. A method for supplying operating power to an X-ray image sensor in connection with an imaging arrangement, said arrangement including imaging means including an x-radiation source and the sensor, which sensor comprises a sensor housing and sensor electronics, said sensor electronics including a receiver of a wireless energy transmission link, in which method energy required for using the sensor in an imaging event is transmitted to the sensor via said receiver of a wireless energy transmission link in connection with said imaging event such that transmission of energy during said imaging event does not start earlier than when a procedure of positioning of said imaging means for an exposure as part of the imaging event is initiated.

21. A sensor according to claim 11 wherein said receiver of said wireless power transmission link comprises an induction receiver.

22. A sensor according to claim 21 wherein said induction receiver comprises a coil having substantially the same shape as a perimeter of the sensor and situated at least in part in the proximity of edges of the sensor.

23. A sensor according to claim 11 wherein said transmitter for transmitting at least the image data comprises a high-frequency RF transmitter comprising a directional antenna.

24. A base station according to claim 16 wherein said energy transmission link is an induction link.

25. A method according to claim 20 wherein energy is transmitted to the sensor continuously or essentially continuously but with one or more short transmission breaks.

26. A method according to claim 20 wherein energy is transmitted to the sensor until image data detected by the sensor during an exposure is transmitted from the sensor or stored to a memory arranged in the sensor.

27. A method according to claim 20 wherein said energy transmission link is an induction link.

28. A method according to claim 20 wherein said energy transmission link is also used as a data transmission link at least for transmitting data to the sensor.

29. A method according to claim 20 wherein data related to controlling operation of the sensor is transmitted to the sensor, said data including a command for re-transmitting at least part of image data detected by the sensor during an exposure.

* * * * *